(12) United States Patent
Smeekens et al.

(10) Patent No.: US 7,449,290 B2
(45) Date of Patent: Nov. 11, 2008

(54) METHOD FOR SELECTING GENETICALLY TRANSFORMED CELLS

(75) Inventors: Josephus Christianus Maria Smeekens, Driebergen (NL); Henriette Schlüpmann, Gouda (NL)

(73) Assignee: Expressive Research B.V., Wageningen (NL)

( * ) Notice: Subject to any disclaimer, the term of this patent is extended or adjusted under 35 U.S.C. 154(b) by 428 days.

(21) Appl. No.: 10/494,651

(22) PCT Filed: Nov. 6, 2002

(86) PCT No.: PCT/EP02/12478

§ 371 (c)(1),
(2), (4) Date: Nov. 23, 2004

(87) PCT Pub. No.: WO03/040377

PCT Pub. Date: May 15, 2003

(65) Prior Publication Data

US 2005/0084971 A1     Apr. 21, 2005

(30) Foreign Application Priority Data

Nov. 6, 2001  (NL) .................................... 1019308

(51) Int. Cl.
*C12Q 1/68* (2006.01)
(52) U.S. Cl. .......................................... 435/6; 435/468
(58) Field of Classification Search ........................ None
See application file for complete search history.

(56) References Cited

FOREIGN PATENT DOCUMENTS

| WO | WO A 93 05163 | 3/1993 |
|---|---|---|
| WO | WO A 94 20627 | 9/1994 |
| WO | WO 96 31612 | 10/1996 |

OTHER PUBLICATIONS

Roger A. Aeschbacher et al., *Purification of the Trehalase GMTREI From Soybean Nodules and Cloning of Its cDNA GMTREI Is Expressed at a Low Level in Multiple Tissue*, Plant Physiology, Feb. 1999, vol. 119, pp. 489-495.

Joachim Muller et al., *Trehalose and Trehalase in Arabidopsis*, Plant Physiology, Feb. 2001, vol. 125, pp. 1086-1093.

Naoki Asano et al., *Effect of Validamycins on Glycohydrolases of Rhizoctonia Solani*, The Journal of Antibiotices, Apr. 1987, pp. 526-532.

Irene Knuesel et al., *Comparative Studies of Suidatrestin, A Specific Inhibitor of Trehalases*, Comparative Biochemistry and Physiology Part B 120, 1998, pp. 639-646.

Reinhold et al., Characterization of a Cytoplasmic Trehalase of *Escherichia coli*, Journal of Bacteriology, Nov. 1996, p. 6250-6257.

*Primary Examiner*—James S Ketter

(57) ABSTRACT

An environmental friendly and non toxic method for selection of transformed cells from a population consisting of transformed and non-transformed cells. The method comprises the following steps a) introducing into a cell at least one desired nucleotide sequence and at least one selection-nucleotide sequence to obtain a genetically transformed cell, wherein the selection-nucleotide sequence comprises a region which codes for a protein involved in the metabolizing of trehalose; b) placing a population with transformed and non-transformed cells into contact with trehalose and/or derivative thereof; and c) selecting the transformed cells from the population on the basis of the capacity of the transformed cells to metabolize the trehalose and/or derivative.

11 Claims, 6 Drawing Sheets

100mM trehalose 100 mM mannitol atgctcaatcagaaaattcaaaaccctaatccagacgaactgatgatcgaagtcgatctctgctatgagctggacccgta
tgaattaaaactggatgagatgatcgaggcagaaccggaacccgagatgattgaagggctgcctgcctctgatgcgctga
cgcctgccgatcgctatctcgaactgttcgagcatgttcagtcggcgaaaattttcccccgacagtaaaacctttcccgac
tgcgcacctaaaatggacccgctggatatcttaatccgctaccgtaaagtgcgccgtcatcgtgattttgacttgcgcaa
gtttgttgaaaaccacttctggctgccggaggtctactccagcgagtatgtatcggacccgcaaaattccctgaaagagc
atatcgaccagctgtggccggtgctaacccgcgaaccacaggatcacattccgtggtcttctctgctggcgctgccgcag
tcatatattgtcccgggcggccgtttagcgaaacctactattgggattcctatttcaccatgctggggctggcggaaag
tggtcgggaagatttgctgaaatgcatggccgataacttcgcctggatgatcgaaaactacggtcacatccccaacggca
accgcacctattatttgagccgctcgcaaccaccggttttttgcgctgatggtggagttgtttgaagaagatggtgtacgc
ggtgcgcgccgctatctcgaccaccttaaaatggaatatgccttctggatggacggtgcagaatcgttaatccctaatca
ggcctatcgccatgttgtgcggatgccggacggatcgctgctcaaccgttactgggacgatcgcgacacgccgcgtgacg
aatcctggcttgaggacgttgaaaccgcgaaacattctggtcgcccgcccaacgaggtgtaccgcgatttacgcgcggggg
gcggcctccggttgggattactcttcccgttggctgcgtgatactggtcgtctggcgagcattcgtaccacccagttcat
ccccatcgatctgaatgccttcctgtttaaactggagagcgccatcgccaacatctcggcgctgaaaggcgagaaagaga
cagaagcactgttccgccagaaagccagtgcccgtcgcgatgcggtaaaccgttacctctgggatgatgaaaacggcatc
taccgcgattacgactggcgacgcgaacaactggcgctgttttccgctgccgccattgtgccactctatgtcggtatggc
gaaccatgaacaggccgatcgtctggcaaacgccgtgcgcagtcggttactgacacctggcgggattctggcaagcgagt
acgaaaccggtgaacagtgggataaacccaacggctgggcaccgttacaatggatggcgattcagggatttaaaatgtac
ggcgatgaccttctgggtgatgaaatcgcgcgaagctggctgaagacggtgaatcagttctatctggaacagcacaaaact
gatcgaaaaataccatattgccgatggtgttccccgcgaaggcggcggtggcgagtatccgttgcaggatgggtttggct
ggactaacggtgtggtacgccgtttaattggtttgtacggcgaaccataa

FIG. 4 atgttggactcggacacagacacggactcaggtcctgtggttgcaacaaccaaactcgtcactttcctccagcgtgtgca
gcacacggcacttcgatcatacactaaaaaacaaacgcctgatcccaaatcctacattgatctatctctcaaacgtccct
acagtctctccaccatcgaatcagccttcgatgatctcacgagcgggtcacatgaccagccagtgccagtggagacgctt
gaaaagttcgtcaaggaatatttcgacggtgcaggggaggatctgctgcaccacgaaccagtagatttcgtctcagatcc
ctccggcttcctctccaacgtggagaacaaagaagtcagagaatgggcgcgtgaggtacacggtctttggagaaatctga
gctgcagagtctctgactcagtaagagagtctgccgaccggcacacgcttctaccgttgccggaaccggttatcattccc
ggttcgagattcagagaagtctattactgggattcttattgggtcatcaaaggacttatgacgagtcaaatgttcactac
cgccaaaggtttagtgacgaatctgatgtcacttgtggagacttatggttacgctttgaacggtgctagagctcattata
ctaacagaagccaaccacctttgttgagctccatggtctatgaaatttataatgtgacaaaagatgaagaacttgtgagg
aaagcaatccctctgcttctcaaagagtacgagttttggaactcaggaaaacataaagtggttattcgagacgctaatgg
ttatgatcacgttttgagccgttattatgctatgtggaacaagccaaggcctgaatcctctgttttcgatgaagaatctg
cttcagggttctcgactatgttagagaaacaacggttccatcgagatatagccacggctgctgaatcaggatgcgatttc
agcacgcgatggatgagggatcctcctaatttcacaacgatggctacaacatcagtggttcctgttgatctaaatgtttt
tcttctcaagatggaactcgatatagcgttcatgatgaaggtttctggagatcaaaatggttcagaccgttttgtgaaag
cgtcaaaagcgagagagaaagcgtttcaaaccgtgtttggaacgagaaagcagggcaatggctggattactggctttcc
tccagtggtgaggaatctgagacatggaaggctgagaaccaaaacaccaacgtctttgcgtctaactttgcaccaatctg
gattaattccatcaattcagatgatgaaaatcttgtcaagaaagttgtgacagctcttaagaactcagggctcattgctc
ccgctggaatcctaacttctttagcaaactcaggacaacaatgggattctccgaatggatgggcaccgcaacaagagatg
atcgtcacagggctcggaagatcgagtgtaaaagaagctaaagagatggcagaggatattgcaaggagatggatcaaaag
caactatcttgtctacaagaaaagtgggactatacatgagaagctcaaagttacagagcttggtgaatatggtggtggag
gagaatatatgccacagaccggattcggatggtcaaatggagttatcttagcattcttggaggaatatggatggccctct
catcttagcattgaagcctag

```
atggcatcacactgtgtaatggccgtgacgccctcaaccctcttctctccttcctcgaacgcctccaagaaacagcctt
cgaaaccttcgcccattccaacttcgatcccaaaacctacgtggacatgcctctcaagtccgccctcacgattaccgagg
acgcgttccagaagcttccgaggaacgccaacgggtccgtgccggttgaggatttgaagcgtttcatagaagcctacttt
gaaggtgcaggggatgatctggtgtaccgggacccacaggatttcgttcccgagccggagggtttcttgcccaaggtgaa
ccaccctcaggttagggcctgggccttgcaggtccattcactttggaaaaaacttgagccggaaaatatccggtgcggtga
aggcacagccagacttacatacgctgctccctctccctggttcggttgtcattcccgggtcgcgttttcgcgaggtttat
tactgggattcctattgggttattaggggcctgctggccagtcaaatgcatgacacagctaaggctattgtcaccaatct
catttccttgatagataaatatggctttgttcttaatggggctagagcttactacactaacaggagccagcctcccctt
taagcgccatgatttatgagatatacaatagcacgggtgacgtggaattagttaaaagatctctacctgccttactgaaa
gaatatgaattttggaattcagatatacataaactgaccattttggatgctcaaggttgcactcataccttaaatcgtta
ttatgcaaagtgggacaaacccaggccggaatcgtccataatggacaaggcatctgcttccaacttctccagtgtttcag
aaaaacagcagtttttaccgtgaactggcatcagctgctgaatcaggatgggatttcagcaccagatggatgagaaatcca
cctaatttcacaacattggctacaacatctgtaatacctgttgatttgaacgcatttctactcgggatggaacttaatat
tgccttatttgcaaaagttactggagataatagcactgctgaacggttcctggaaaattctgatcttagaaagaaggcaa
tggactctatttctggaatgcaaacaagaaacagtggcttgattactggctcagcagtacatgtgaggaggttcatgtt
tggaaaaaacgagcatcagaatcaaaatgtatttgcttccaatttttgttcctttgtggatgaagccatttactcagatac
ttcgcttgtgagtagtgttgttgaaagtctcaaaacatctggcctgctccgtgatgctggagttgcaacttctttgactg
attcagggcaacagtgggactttccaaatgggtgggcgccgcttcaacacatgctagtggaaggactgctaaaatcagga
ttgaaagaagcaaggttattggctgaggaaattgccatcagatgggtcacaaccaattatattgtttataagaaaacagg
tgtaatgcatgaaaagtttgacgtggagcattgtggagaatttggaggtgggggcgaatatgtaccccagactggttttg
gctggtcaaatggagttgtgttggcattcttggaggagtttggatggcctgaagatcggaacatagaatgttga
```

FIG. 6

METHOD FOR SELECTING GENETICALLY TRANSFORMED CELLS

FIELD OF THE INVENTION

The present invention relates to a method for selecting genetically transformed cells.

BACKGROUND OF THE INVENTION

It is known that when genetic material is introduced into a population of cells by means of transformation, only a number of the cells will be transformed successfully. After transformation the transformed cells must be identified and selected from a population of transformed and non-transformed cells. A selection gene is therefore generally also introduced into the cell for this purpose in addition to the desired transgene. The selection gene herein codes for instance for a property with which the genetically transformed cells can be identified. Examples of such selection genes are for instance genes which code for resistance to antibiotics or herbicides. After the transformation the population of transformed and non-transformed cells is brought into contact with the antibiotic or herbicide toxic for the non-transformed ("wild-type") cells, so that only the transformed cells are able to survive and grow due to the presence of the introduced selection gene.

The use of such selection genes which code for antibiotic- or herbicide-resistance is however not generally desirable for transgenic crops which are introduced on a large scale into the environment, and particularly in food crops. Another drawback of such a selection mechanism is further for instance that the non-transformed cells will generally die off, and moreover that when the population of cells is a coherent tissue of cells or a whole organism, the transformed cells can also die as a result of for instance harmful compounds secreted by the dying, non-transformed cells.

The object of the present invention is to provide a method for selecting transformed cells from a population of transformed and non-transformed cells, wherein the above stated drawbacks are obviated.

BRIEF DESCRIPTION OF THE INVENTION

This object is achieved with the invention by providing a method comprising of:
a) introducing into a cell at least one desired nucleotide sequence and at least one selection-nucleotide sequence to obtain a genetically transformed cell, wherein the selection-nucleotide sequence comprises a region which codes for a protein involved in the metabolizing of trehalose;
b) placing a population with transformed and non-transformed cells into contact with trehalose and/or derivative thereof; and
c) selecting the transformed cells from the population on the basis of the capacity of the transformed cells to metabolize the trehalose and/or derivative.

DETAILED DESCRIPTION OF THE INVENTION

Trehalose is het α-1,1-disaccharide of glucose which is produced by many organisms, including bacteria, yeasts and fungi, as well as several higher plants. It is the most important blood sugar in insects. Trehalose is increasingly being used for among other things the preparation of vaccines and in organ transplant protocols because it provides protection against protein denaturation and membrane damage.

Cells, in particular plant cells, can not normally develop in a medium in which an increased concentration of trehalose is present without another metabolizable carbon source being present. In the method according to the invention use is made hereof to select transformed cells. For this purpose the cells, in addition to using the desired transgene, are also transformed with a selection-nucleotide sequence, wherein the selection-nucleotide sequence comprises a region which codes for a protein which is involved in the metabolizing of trehalose. A population with transformed and non-transformed cells are then brought into contact with trehalose and/or a derivative thereof, for instance by adding trehalose and/or derivative thereof to the culture medium. The transformed cells are thus distinguished from the non-transformed cells not only by the relevant introduced transgene but also by the presence of a nucleotide sequence in their genome which codes for a protein which can metabolize the trehalose. The transformed cells will hereby be able to survive and grow in the medium with trehalose and/or derivative of trehalose, while the non-transformed cells will not develop further. In this manner the transformed cells can thus be selected from the total population of cells on the basis of their capacity to metabolize the trehalose and/or derivative.

The term "protein involved in the metabolizing of trehalose" relates herein to a protein, for instance an enzyme, which is able to break down trehalose and/or the derivative thereof, and thereby reduce the concentration of trehalose and/or derivative.

The term "derivative of trehalose" relates to modified forms of trehalose which can also be metabolized by the relevant protein and induce the same response in the cells as trehalose, such as for instance methylated or halogenated forms of trehalose.

In a preferred embodiment of the method according to the invention the introduced selection-nucleotide sequence comprises a region which codes for an intracellular protein with trehalase activity, i.e. an enzyme able to hydrolyze intracellular trehalose and/or derivative thereof to glucose. Owing to the presence of this protein in the transformed cells, and the absence thereof in the non-transformed cells, only the transformed cells will be able to break down the trehalose and/or derivative which enters the cell. The intracellular concentration of the trehalose in the transformed cells is hereby reduced, while the released glucose can moreover be used by the transformed cells as extra nutrient source.

Many cells, in particular cells of higher plants, such as *Glycine max.* and *Arabidopsis thaliana*, have in their genome the gene for an endogenous trehalase (Aeschbacher R. A. et al., Plant Physiol. 119(2): 489-496, 1999; Mueller et al. Plant Physiol. 125(2): 1086-1093, 2001). However, these endogenous trehalase genes generally code for an extracellular trehalase, which is not active in the cell. It is possible to modify such endogenous genes using standard molecular biological techniques. In a preferred embodiment of the method according to the invention the selection-nucleotide sequence therefore comprises a modified endogenous trehalase gene which codes for an intracellularly active trehalase. The endogenous trehalase gene is herein modified such that the trehalase which is expressed is intracellularly active, such as for instance by deactivating the protein-secretion signal via deletion or mutagenesis, by changing the protein targeting sequences, or the pH sensitivity of the enzymatically active site.

In a particularly suitable embodiment of the method according to the invention the introduced selection-nucleotide sequence comprises the TreF gene from *E. coli* (Horlacher R. et al., J. Bacteriol. 178(1): 6250-6257, 1996). This gene is simple to isolate and to introduce into diverse cells using standard molecular biological techniques.

In another advantageous embodiment of the invention the selection-nucleotide sequence comprises the AtTRE1 gene from *Arabidopsis* (Locus At4G24040, AGI no. 2134960).

The method according to the invention preferably further comprises of also bringing the population of cells in contact with at least one inhibitor of endogenous extracellular trehalase before or during step b). Inhibition of the possibly present endogenous extracellular trehalase prevents the trehalose from the medium already being partly or wholly broken down outside the cells, whereby the non-transformed cells would also be able to develop further.

Examples of suitable inhibitors for use in the method according to the invention are suidatestrin and a modified form of the pseudo-oligosaccharide antibiotic validamycin (Asano N. et al., J. Antibiot. 40(4): 526-532, 1987; Goddijn O. J. et al., Plant Physiol. 113(1): 181-190, 1997; Knuesel I. et al., Comp. Biochem. Physiol. B. Biochem. Mol. Biol. 120(4): 639-646, 1998). The validamycin must herein be modified such it can no longer enter the cell. Other compounds which inhibit the activity of endogenous extracellular trehalase and which are not taken up into the cell can however also be used according to the invention.

The term "population of cells" is understood to mean according to the invention a population of individual cells, as well as cells in tissues and organs or parts thereof; or cells in whole organisms such as for instance plants, wherein the whole plants or parts thereof can consist of the genetically transformed cells.

The method according to the invention is preferably used to select genetically modified plant cells. Seedlings of for instance *Arabidopsis* cannot develop further on media containing increased concentrations of trehalose. While seeds will germinate, the formation of an extensive root system and the development of the first leaf stage are inhibited by the presence of trehalose. Because the genetically transformed plants are able to express a trehalase, particularly in the cytoplasm of the cell, due to the introduction of the selection-nucleotide sequence, the trehalose which enters the cell can be broken down to glucose. The glucose can then be used as nutrient source for the plant. The genetically transformed plants will therefore develop further, while the development of the non-transformed plants lags behind. When the method according to the invention is used for the selection of genetically transformed cells in plants, the transformed plants can readily be identified visually.

The method according to the present invention therefore provides a simple, environmentally-friendly selection system for transformed cells, particularly for genetically transformed plants. Trehalose is a simple compound which is relatively inexpensive te produce and which has moreover been found to be non-toxic for humans and animals. Humans have thus been consuming large quantities of trehalose for a long time in products of yeast fermentation such as bread and beer, and humans and animals are continually exposed to trehalose due to the presence of trehalose-producing microbes in the intestinal flora.

According to the invention any nucleotide sequence which codes for a protein with trehalase activity can be used as selection-nucleotide sequence in the genetically transformed cells. Use can for instance be made of exogenous trehalase genes, such as for instance come from bacteria such as *E. coli*, although use can also be made of endogenous trehalase genes, wherein the genes are modified such that they code for modified forms of the endogenous trehalase, for instance for an intracellular form of the normally only extracellularly active trehalase. The advantage of using such endogenous trehalase genes is that no additional foreign genetic material is introduced into the cell.

The desired transgene and the selection-nucleotide sequence can be introduced into the cell for transforming using standard molecular-biological techniques. Although this is not essential, the transgene and selection gene can herein be linked to each other so that the presence of the selection gene always signifies that the transgene is also present. The transgene and the selection gene can optionally form part of the same genetic construct and be introduced via the same vector into the cell. In order to ensure that the selection-nucleotide sequence is expressed in the transformed cells, such a genetic construct will further also comprise regulatory sequences such as for instance a constitutive or regulatable promotor.

The method according to the invention can be used in particularly suitable manner to select transgenic plants. Examples of plants for which the method according to the invention-can be used are for instance maize (*Zea mays* L.), wheat (*Triticum aestivm* L.), barley (*Hordeum vulgare* L.), rice (*Oryza sativa* L.), soyabean (*Phaseolus vulgaris* L.), sugar beet (*Beta vulgaris* L.), chicory (*Cichorum intybus* L.), rapeseed (*Brassica napus* L.), sugar cane (*Saccharum officinarum* L.), sweet potato (*Diocorea esculenta* L.), manioc (*Manihot esculenta* L.), potato (*Solanum tuberosum* L.), tomato (*lycopersicon esculentum* L.) and grasses (for instance *Lolium* ssp. *Poa* spp. and *Festuca* spp.).

The present invention further relates to the transformed cells which are selected using the method according to the invention, in particular plant cells, and to the plants regenerated therefrom, and their seeds and progeny.

The invention is further elucidated with reference to the accompanying examples and figures.

FIG. 1 shows the sensitivity of two different accessions of *Arabidopsis thaliana* to trehalose. A: seeds cultured in the presence of 100 mM mannitol (control); B: seeds cultured in the presence of 100 mM trehalose.

FIG. 4 shows the nucleotide sequence of the TreF gene from *E. coli*.

FIG. 5 shows the mRNA sequence of *Arabidopsis thaliana* AtTre1.

FIG. 6 shows the mRNA sequence of GMTre1 from *Glycine max*.

EXAMPLES

Example 1

Sensitivity to Trehalose of Seedlings of *Arabidopsis thaliana* Col. O and La-er Seeds were sterilized using the gas-phase protocol of Clough and Bent (1998) (Clough S. J., Bent A. F., Plant J. 16(6): 735-743, 199.8) in Eppendorf tubes. The sterilized sees were then resuspended in sterile water and arranged on 0.8% w/v agar medium containing half-strength Murashigue and Skoog medium (MS medium; Murashigue T, Skoog F, Physiol. Plant. 15: 473-497, 1977), vitamins and MES buffer (pH 5.7), supplemented with mannitol or trehalose in a final concentration of 100 mM.

Figure 1B:
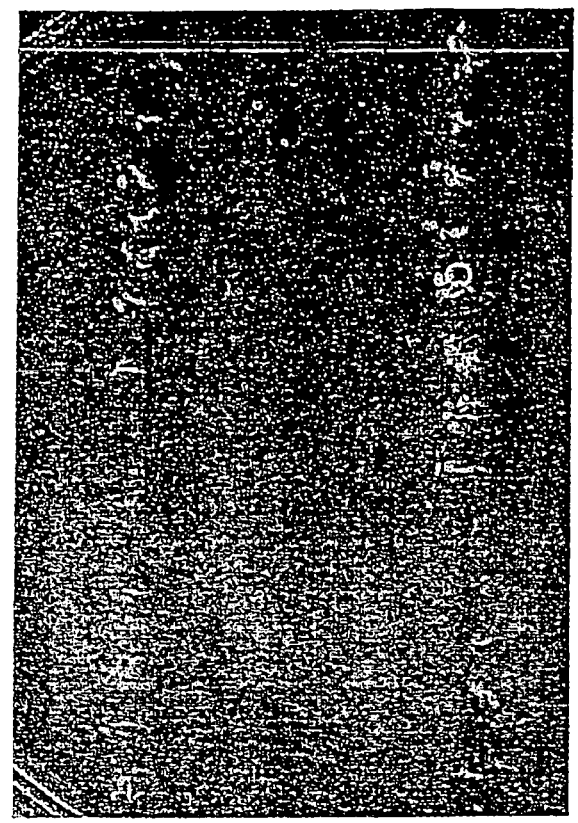
Figure 1A:
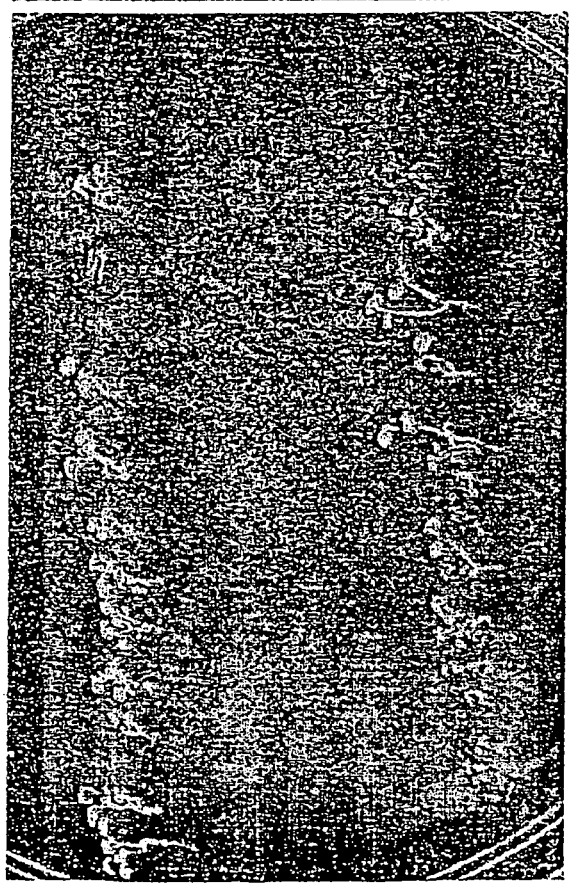

The seeds cultured in the presence of 100 mM mannitol developed into plants with an extensive root system, while a lesser development was observed in the plants cultured in the presence of 100 mM trehalose, as shown in FIG. 1. FIG. 1A herein shows the seeds cultured in the presence of 100 mM mannitol (control) and FIG. 1B the seeds cultured in the presence of 100 mM trehalose.

The upper row of plants are the *Arabidopsis thaliana* Landsberg erecta (La-er), and the lower row of plants are the *Arabidopsis thaliana* Colombia (Col.O).

Example 2

Expression Vectors with the *E. coli* Cytoplasmic Trehalase Gene (TreF) as Selection Gene TreF was amplified from the genomic DNA of *E. coli* using the PCR-primers Treld (CTC TGC AGA TGC TCA ATC AGA AAA TTC AAA ACC) (SEQ ID NO:4) and Trelu (TGC ACT GCA GTT ATG GTT CGC CGT ACA AAC CAA) (SEQ ID NO:5). The amplified TreF was then cloned in the pGEMT vector (Promega, US). The TreF gene was further modified for the introduction of a myc-tag at the C-terminal end of the protein using the PCR primers TRe2d (AGC ACT GCA GCC ATG GCT TTG GTT ACC CTC AAT CAG AAA ATT CAA AAC CCT) (SEQ ID NO:6) and Tremyc (TTA CAG ATC TTC TTC AGA AAT AAG TTT TTG TTC TGG TTC GCC GTA CAA ACC AAT TAA) (SEQ ID NO:7) and again cloned in pGEMT for sequence validation. The resulting modified TreF sequence was cut with Pst1 restriction enzyme and introduced into:

A. pCAMBIA2201 (CAMBIA, Australia). The outer ends of the TreF fragment were blunted and the fragment ligated in pCAMBIA220 plasmid digested and blunted with NcoI and BstEII.

B. Pst1 site of pCambia 2380; for this purpose the ubiquitin 10 promotor of *Arabidopsis thaliana* was added as blunted Xho1-Spe 1 fragment in the blunted HindIII site of pcambia 2380-TreF.

C. Pst1 site of the pACN plasmid (Zeneca, Caddick M. X. et al., Nat. Biotechnol. 16(2): 177-180, 1998). The resulting construct was then digested with HindIII, wherein a fragment was released having thereon the hybrid AlcA/minimal 35S promotor, followed by the TreF sequence and the Nos PolyA terminator. This fragment was inserted into the HindIII site of the SRN binary vector (Zeneca), whereby the shown construct was obtained.

Figure 2:
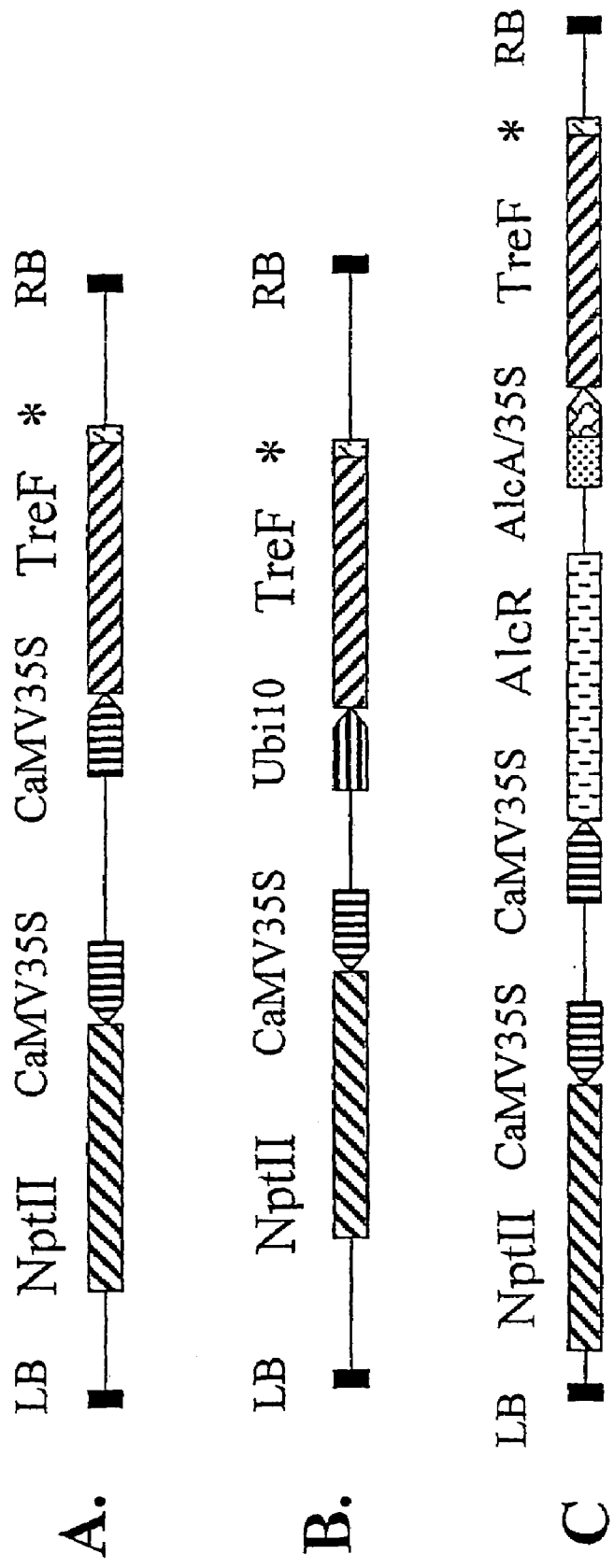
FIG. 2 shows different constructs for cytoplasmic expression of the *E. coli* trehalase gene.

FIG. 2 shows the obtained constructs. LB: left T-DNA boundary; RB: right T-DNA boundary; treF: *E. coli* gene coding for the cytoplasmic trehalase; NptII: neomycin phosphotransferase gene II: AlcR: gene coding for regulator of the alcohol inducable system; CaMV35S: cauliflower mosaic virus 35S promotor; Ubi10: promotor of the ubiquitin 10 gene of *Arabidopsis thaliana*; AlcA/35S: AlcA promotor element reacting to ethanol induction, fused with the CaMV35S promotor.

Example 3

Selection of Transgenic *Arabidopsis* Seedlings

*Arabidopsis thaliana* Col.O plants were transformed with Aarobacterium with the binary plasmid as described in Example 2C, via the "floral dip" protocol (Clough and Bent, supra). The obtained dry seeds were sterilized and sown on 0.8% w/v solid agar medium having therein half-strength MS-salts (½ MS-salts), vitamins and MES buffer pH 5.7, supplemented with trehalose in a final concentration of 100 mM. The dishes were incubated for 3 days at 4° C. (stratification), whereafter a drop of ethanol was applied to the inside of the cover and dishes were transferred to 22° C.

Figure 3:
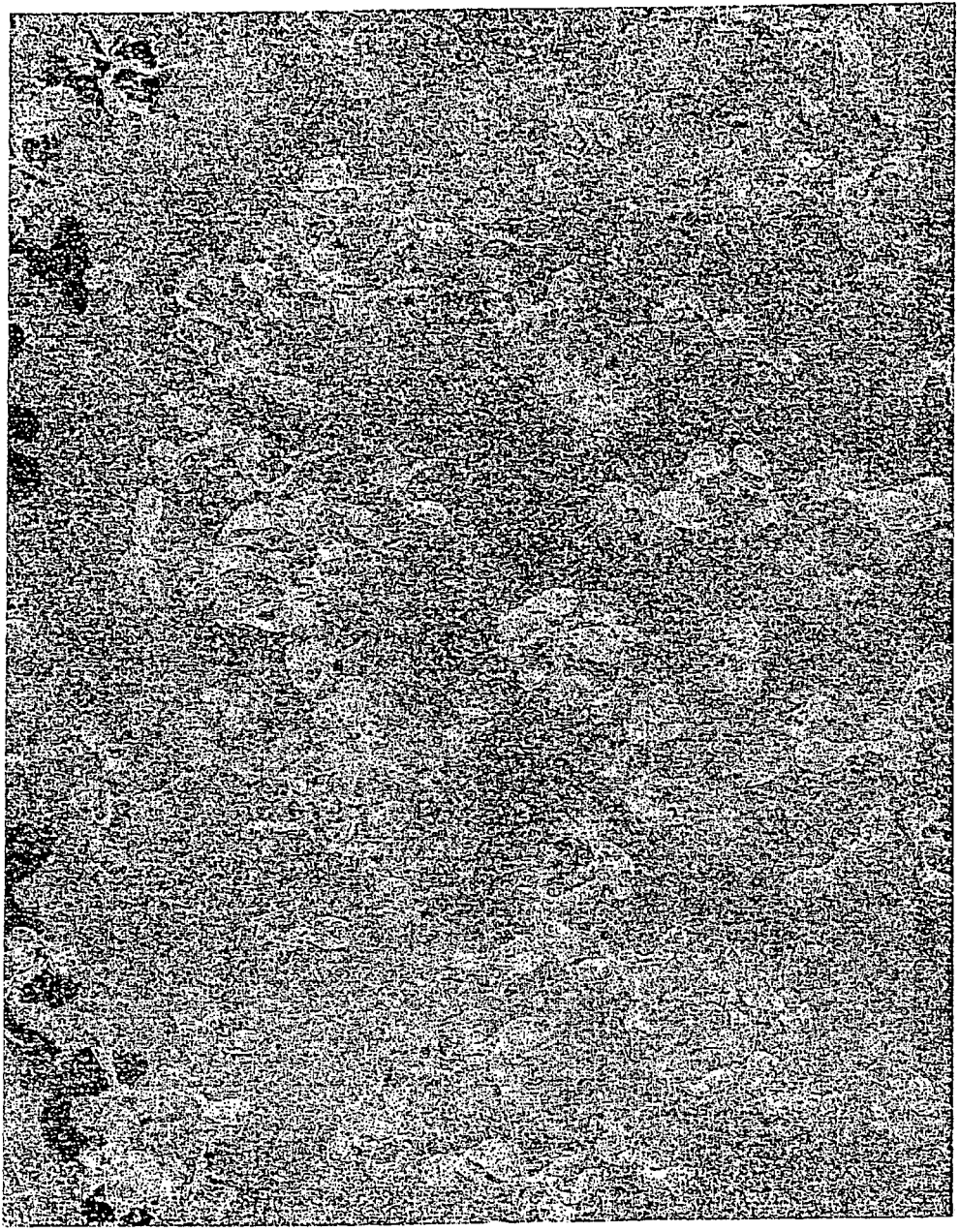
FIG. 3 shows a culture of transformed and non-transformed *Arabidopsis thaliana* Col.O seedlings in the presence of 100 mM trehalose.

FIG. 3 shows the seedlings obtained after 12 days. The transformed resistant seedlings are green, have long roots and primary leaves. The non-transformed, sensitive seedlings on the other hand accumulate anthocyanins, develop no primary leaves and the roots do not become longer than 3 mm. In moist conditions the cotyledons become pale.

Of the approximately 4000 sown plants, 24 resistant seedlings were identified. This shows that the transformation-frequency is comparable to that obtained with other selection systems. Twelve seedlings were transferred to black earth and developed into plants which could not be distinguished from non-transformed wild-type plants.

Example 4

Stable Expression of the Trehalase-Coding Selection Gene in *Arabidopsis* Transgenic Lineages The stability of the expression of the selection gene coding for trehalase was tested in independent *Arabidopsis* transgenic lineages using the conventional kanamycin selection gene linked to the selection gene according to the invention.

T2 seeds obtained from ten self-pollinated T1 plants from Example 3 were sterilized and sown on 0.8% solid agar medium having therein ½MS-salts, supplemented with 1% w/v sucrose and 25 mg/l kanamycin, incubated for 3 days at 4° C., transferred to 22° C. and grown for 12 days in a 16-hour light/8-hour dark cycle. The germination frequency was 100%.

Kanamycin-sensitive seedlings germinated but had blanched cotyledons, no root development and no primary leaf stage. Kanamycin-resistant seedlings were green, developed primary leaves and roots.

As shown in table 1, the transgenic construct of the T1 plants was always passed on to the T2 generation. Table 1 shows the number of seedlings resistant to kanamycin in each tested lineage.

*Arabidopsis* produces seeds through self-fertilization and is a diploid plant. When the T1 generation plant has at least one stable transgene in its genome, the T2 generation will consist of at least ¾ resistant plants and a maximum of ¼ sensitive plants. When the transgene is not inserted in stable manner in the genome of the T1 plants, the transgene will not be found in the T2 generation. Table 1 shows that, by making use of kanamycin-selection on the T2 generation, T2 seedlings with the transgene can be found in each T1 lineage.

TABLE 1

| Ti lineage | kanamycin-sensitive seedlings | kanamycin-resistant seedlings |
|---|---|---|
| TF1 | 5 | 23 |
| TF2 | 3 | 7 |
| TF4 | 21 | 54 |
| TF5 | 14 | 48 |
| TF7 | 24 | 65 |
| TF8 | 13 | 42 |
| TF9 | 0 | 80 |
| TF10 | 9 | 28 |
| TF11 | 10 | 47 |
| TF12 | 15 | 54 |

The invention claimed is:

1. Method for selecting genetically transformed cells from a population of cells, comprising of
   a) introducing into a cell at least one desired nucleotide sequence and at least one selection-nucleotide sequence to obtain a genetically transformed cell, wherein the selection-nucleotide sequence comprises a region which codes for a protein involved in the metabolizing of trehalose, wherein protein has trehalase activity;
   b) placing a population with transformed and non-transformed cells into contact with trehalose and/or methylated or halogenated forms of trehalose; and
   c) selecting the transformed cells from the population on the basis of the capacity of the transformed cells to metabolize the trehalose and/or methylated or halogenated forms of trehalose.

2. Method as claimed in claim 1, characterized in that the selection-nucleotide sequence comprises a modified endogenous trehalase gene which codes for an intracellularly active trehalase.

3. Method as claimed in claim 1, characterized in that the selection-nucleotide sequence comprises the TreF gene from *E. Coli*.

4. Method as claimed in claim 1, characterized in that the selection-nucleotide sequence comprises the AtTRE1 gene from *Arabidopsis*.

5. Method as claimed in claim 1, characterized in that the method further comprises of:
   also bringing the population of cells into contact with at least one inhibitor of endogenous extracellular trehalase before or during step b).

6. Method as claimed in claim 1, characterized in that the cell is a plant cell.

7. Method for using trehalose and/or a methylated or halogenated forms of trehalose for the selection of transformed cells from a population of transformed and non-transformed cells, wherein the genome of the transformed cells comprises at least one selection-nucleotide sequence comprising a region which codes for a protein involved in the metabolizing of trehalose and the selection-nucleotide sequence comprises a region which codes for an intracellular protein with trehalase activity.

8. Method according to claim 7, characterized in that the selection-nucleotide sequence comprises a modified endogenous trehalase gene which codes for an intracellularly active trehalase.

9. Method according to claim 7, characterized in that the selection-nucleotide sequence comprises the TreF gene from *E. Coli*.

10. Method according to claim 7, characterized in that the selection-nucleotide sequence comprises the AtTRE1 gene from *Arabidopsis*.

11. Method according to claim 7, characterized in that the cell is a plant cell.

* * * * *

UNITED STATES PATENT AND TRADEMARK OFFICE
CERTIFICATE OF CORRECTION

| | |
|---|---|
| PATENT NO. | : 7,449,290 B2 |
| APPLICATION NO. | : 10/494651 |
| DATED | : November 11, 2008 |
| INVENTOR(S) | : Smeekens et al. |

It is certified that error appears in the above-identified patent and that said Letters Patent is hereby corrected as shown below:

Column 13, Line 27, Claim 1, "wherein protein" should read -- wherein the protein --

Signed and Sealed this

Seventeenth Day of March, 2009

JOHN DOLL
*Acting Director of the United States Patent and Trademark Office*

SEQUENCE LISTING

<160> NUMBER OF SEQ ID NOS: 7

<210> SEQ ID NO 1
<211> LENGTH: 1650
<212> TYPE: DNA
<213> ORGANISM: Escherichia coli
<220> FEATURE:
<221> NAME/KEY: misc_feature
<223> OTHER INFORMATION: E. coli TreF (fig. 4); GI:466582

<400> SEQUENCE: 1

| | | | | | |
|---|---|---|---|---|---|
| atgctcaatc | agaaaattca | aaccctaat | ccagacgaac | tgatgatcga | agtcgatctc | 60 |
| tgctatgagc | tggacccgta | tgaattaaaa | ctggatgaga | tgatcgaggc | agaaccggaa | 120 |
| cccgagatga | ttgaagggct | gcctgcctct | gatgcgctga | cgcctgccga | tcgctatctc | 180 |
| gaactgttcg | agcatgttca | gtcggcgaaa | attttccccg | acagtaaaac | ctttcccgac | 240 |
| tgcgcaccta | aaatggaccc | gctggatatc | ttaatccgct | accgtaaagt | gcgccgtcat | 300 |
| cgtgattttg | acttgcgcaa | gtttgttgaa | aaccacttct | ggctgccgga | ggtctactcc | 360 |
| agcgagtatg | tatcggaccc | gcaaaattcc | ctgaaagagc | atatcgacca | gctgtggccg | 420 |
| gtgctaaccc | gcgaaccaca | ggatcacatt | ccgtggtctt | ctctgctggc | gctgccgcag | 480 |
| tcatatattg | tcccgggcgg | ccgttttagc | gaaacctact | attgggattc | ctatttcacc | 540 |
| atgctggggc | tggcggaaag | tggtcggaa | gatttgctga | aatgcatggc | cgataacttc | 600 |
| gcctggatga | tcgaaaacta | cggtcacatc | cccaacggca | accgcaccta | ttatttgagc | 660 |
| cgctcgcaac | caccggtttt | tgcgctgatg | gtggagttgt | ttgaagaaga | tggtgtacgc | 720 |
| ggtgcgcgcc | gctatctcga | ccaccttaaa | atggaatatg | ccttctggat | ggacggtgca | 780 |
| gaatcgttaa | tccctaatca | ggcctatcgc | catgttgtgc | ggatgccgga | cggatcgctg | 840 |
| ctcaaccgtt | actgggacga | tcgcgacacg | ccgcgtgacg | aatcctggct | tgaggacgtt | 900 |
| gaaaccgcga | acattctgg | tcgcccgccc | aacgaggtgt | accgcgattt | acgcgcgggg | 960 |
| gcggcctccg | gttgggatta | ctcttcccgt | tggctgcgtg | atactggtcg | tctggcgagc | 1020 |
| attcgtacca | cccagttcat | ccccatcgat | ctgaatgcct | tcctgtttaa | actggagagc | 1080 |
| gccatcgcca | catctcggc | gctgaaaggc | gagaaagaga | cagaagcact | gttccgccag | 1140 |
| aaagccagtg | cccgtcgcga | tgcggtaaac | cgttacctct | gggatgatga | aaacggcatc | 1200 |
| taccgcgatt | acgactggcg | acgcgaacaa | ctggcgctgt | tttccgctgc | cgccattgtg | 1260 |
| ccactctatg | tcggtatggc | gaaccatgaa | caggccgatc | gtctggcaaa | cgccgtgcgc | 1320 |
| agtcggttac | tgacacctgg | cgggattctg | gcaagcgagt | acgaaaccgg | tgaacagtgg | 1380 |
| gataaaccca | acggctgggc | accgttacaa | tggatggcga | ttcagggatt | taaaatgtac | 1440 |
| ggcgatgacc | ttctgggtga | tgaaatcgcg | cgaagctggc | tgaagacggt | gaatcagttc | 1500 |
| tatctggaac | agcacaaact | gatcgaaaaa | taccatattg | ccgatggtgt | tccccgcgaa | 1560 |
| ggcggcggtg | gcgagtatcc | gttgcaggat | gggtttggct | ggactaacgg | tgtggtacgc | 1620 |
| cgtttaattg | gtttgtacgg | cgaaccataa | | | | 1650 |

<210> SEQ ID NO 2
<211> LENGTH: 1674
<212> TYPE: DNA
<213> ORGANISM: Arabidopsis thaliana
<220> FEATURE:
<221> NAME/KEY: misc_feature
<223> OTHER INFORMATION: A.thaliana AtTre1 (fig. 5); GI:2262097

<400> SEQUENCE: 2

```
atgttggact cggacacaga cacggactca ggtcctgtgg ttgcaacaac caaactcgtc      60
actttcctcc agcgtgtgca gcacacggca cttcgatcat accctaaaaa acaaacgcct     120
gatcccaaat cctacattga tctatctctc aaacgtccct acagtctctc caccatcgaa     180
tcagccttcg atgatctcac gagcgagtca catgaccagc cagtgccagt ggagacgctt     240
gaaaagttcg tcaaggaata ttttgacggt gcaggggagg atctgctgca ccacgaacca     300
gtagatttcg tctcagatcc ctccggcttc ctctccaacg tggagaacga agaagtcaga     360
gaatgggcgc gtgaggtaca cggtctttgg agaaatctga gctgcagagt ctctgactca     420
gtaagagagt ctgccgaccg gcacacgctt ctaccgttgc cggaaccggt tatcattccc     480
ggttcgagat tcagagaagt ctattactgg gattcttatt gggtcatcaa aggacttatg     540
acgagtcaaa tgttcactac cgccaaaggt ttagtgacga atctgatgtc acttgtggag     600
acttatggtt acgctttgaa cggtgctaga gcttattata ctaacagaag ccaaccacct     660
ttgttgagct ccatggtcta tgaaatttat aatgtgacaa agatgaaga acttgtgagg     720
aaagcaatcc ctctgcttct caagagtac gagtttgga actcaggaaa acataaagtg     780
gttattcgag acgctaatgg ttatgatcac gttttgagcc gttattatgc tatgtggaac     840
aagccaaggc ctgaatcctc tgttttcgat gaagaatctg cttcagggtt ctcgactatg     900
ttagagaaac aacggttcca tcgagatata gccacggctg ctgaatcagg atgcgatttc     960
agcacgcgat ggatgaggga tcctcctaat ttcacaacga tggctacaac atcagtggtt    1020
cctgttgatc taaatgtttt tcttctcaag atggaactcg atatagcgtt catgatgaag    1080
gtttctggag atcaaaatgg ttcagaccgt tttgtgaaag cgtcaaaagc gagagagaaa    1140
gcgtttcaaa ccgtgttttg gaacgagaaa gcagggcaat ggctggatta ctggctttcc    1200
tccagtggtg agaaccaaaa caccaacgtc tttgcgtcta actttgcacc aatctggatt    1260
aattccatca attcagatga aaatcttgtc aagaaagttg tgacagctct taagaactca    1320
gggctcattg ctcccgctgg aatcctaact tctttgacaa actcaggaca acaatgggat    1380
tctccgaatg gatgggcacc gcaacaagag atgatcgtca cagggctcgg aagatcgagt    1440
gtaaaagaag ctaaagagat ggcagaggat attgcaagga gatggatcaa aagcaactat    1500
cttgtctaca gaaaagtgg gactatacat gagaagctca agttacaga gcttggtgaa    1560
tatggtggtg gaggagaata tatgccacag accggattcg gatggtcaaa tggagttatc    1620
ttagcattct tggaggaata tggatggccc tctcatctta gcattgaagc ctag          1674
```

<210> SEQ ID NO 3
<211> LENGTH: 1674
<212> TYPE: DNA
<213> ORGANISM: Glycine max
<220> FEATURE:
<221> NAME/KEY: misc_feature
<223> OTHER INFORMATION: G.max GMTre1 (fig. 6); GI:4559291

<400> SEQUENCE: 3

```
atggcatcac actgtgtaat ggccgtgacg ccctcaaccc ctcttctctc cttcctcgaa      60
cgcctccaag aaacagcctt cgaaaccttc gcccattcca acttcgatcc caaaacctac     120
gtggacatgc tctctcaagtc cgccctcacg attaccgagg acgcgttcca gaagcttccg     180
aggaacgcca acgggtccgt gccggttgag gatttgaagc gtttcataga agcctacttt     240
gaaggtgcag gggatgatct ggtgtaccgg gacccacagg atttcgttcc cgagccggag     300
```

-continued

```
ggtttcttgc ccaaggtgaa ccaccctcag gttagggcct gggccttgca ggtccattca      360
ctttggaaaa acttgagccg gaaaatatcc ggtgcggtga aggcacagcc agacttacat      420
acgctgctcc ctctccctgg ttcggttgtc attcccgggt cgcgttttcg cgaggtttat      480
tactgggatt cctattgggt tattaggggc ctgctggcca gtcaaatgca tgacacagct      540
aaggctattg tcaccaatct catttccttg atagataaat atggctttgt tcttaatggg      600
gctagagctt actacactaa caggagccag cctccccttt taagcgccat gatttatgag      660
atatacaata gcacgggtga cgtggaatta gttaaaagat ctctacctgc cttactgaaa      720
gaatatgaat tttggaattc agatatacat aaactgacca ttttggatgc tcaaggttgc      780
actcatacct taaatcgtta ttatgcaaag tgggacaaac ccaggccgga atcgtccata      840
atggacaagg catctgcttc caacttctcc agtgtttcag aaaaacagca gttttaccgt      900
gaactggcat cagctgctga atcaggatgg gatttcagca ccagatggat gagaaatcca      960
cctaatttca caacattggc tacaacatct gtaatacctg ttgatttgaa cgcatttcta     1020
ctcgggatgg aacttaatat tgccttattt gcaaagtta ctggagataa tagcactgct     1080
gaacggttcc tggaaaattc tgatcttaga aagaaggcaa tggactctat tttctggaat     1140
gcaaacaaga acagtggct tgattactgg ctcagcagta catgtgagga ggttcatgtt     1200
tggaaaaacg agcatcagaa tcaaaatgta tttgcttcca attttgttcc tttgtggatg     1260
aagccatttt actcagatac ttcgcttgtg agtagtgttg ttgaaagtct caaaacatct     1320
ggcctgctcc gtgatgctgg agttgcaact tctttgactg attcagggca acagtgggac     1380
tttccaaatg ggtgggcgcc gcttcaacac atgctagtgg aaggactgct aaaatcagga     1440
ttgaaagaag caaggttatt ggctgaggaa attgccatca gatgggtcac aaccaattat     1500 attgttata gaaaacagg tgtaatgcat gaaaagtttg acgtggagca ttgtggagaa     1560
tttggaggtg ggggcgaata tgtaccccag actggttttg gctggtcaaa tggagttgtg     1620
ttggcattct tggaggagtt tggatggcct gaagatcgga acatagaatg ttga          1674
```

<210> SEQ ID NO 4
<211> LENGTH: 33
<212> TYPE: DNA
<213> ORGANISM: Artificial
<220> FEATURE:
<223> OTHER INFORMATION: Primer Tre1d for amplification of E.coli TreF

<400> SEQUENCE: 4

```
ctctgcagat gctcaatcag aaaattcaaa acc                                     33
```

<210> SEQ ID NO 5
<211> LENGTH: 33
<212> TYPE: DNA
<213> ORGANISM: Artificial
<220> FEATURE:
<223> OTHER INFORMATION: Primer Tre1u for amplification of E.coli TreF

<400> SEQUENCE: 5

```
tgcactgcag ttatggttcg ccgtacaaac caa                                     33
```

<210> SEQ ID NO 6
<211> LENGTH: 51
<212> TYPE: DNA
<213> ORGANISM: Artificial
<220> FEATURE:
<223> OTHER INFORMATION: Primer Tre2d for amplification of E.coli TreF
      and introduction of a myc-tag

```
<400> SEQUENCE: 6
agcactgcag ccatggcttt ggttaccctc aatcagaaaa ttcaaaaccc t          51

<210> SEQ ID NO 7
<211> LENGTH: 57
<212> TYPE: DNA
<213> ORGANISM: Artificial
<220> FEATURE:
<223> OTHER INFORMATION: Primer Tremyc for amplification of E.coli TreF
      and introduction of a myc-tag

<400> SEQUENCE: 7
ttacagatct tcttcagaaa taagtttttg ttctggttcg ccgtacaaac caattaa    57
```